(12) United States Patent
Ra et al.

(10) Patent No.: US 8,808,682 B2
(45) Date of Patent: Aug. 19, 2014

(54) METHOD FOR INDUCING MIGRATION OF ADIPOSE-DERIVED ADULT STEM CELLS

(75) Inventors: Jeong Chan Ra, Gyeonggi-do (KR); Sung Keun Kang, Seoul (KR); Sun Jin Baek, Seoul (KR)

(73) Assignee: RNL Bio Co., Ltd, Seoul (KR)

( * ) Notice: Subject to any disclaimer, the term of this patent is extended or adjusted under 35 U.S.C. 154(b) by 43 days.

(21) Appl. No.: 13/502,898

(22) PCT Filed: Oct. 25, 2010

(86) PCT No.: PCT/KR2010/007329
§ 371 (c)(1),
(2), (4) Date: Jul. 5, 2012

(87) PCT Pub. No.: WO2011/049414
PCT Pub. Date: Apr. 28, 2011

(65) Prior Publication Data
US 2012/0276044 A1    Nov. 1, 2012

(30) Foreign Application Priority Data

Oct. 23, 2009  (KR) ........................ 10-2009-0101117

(51) Int. Cl.
*C12N 5/0775*  (2010.01)
*C12N 5/071*  (2010.01)
*A61K 35/12*  (2006.01)

(52) U.S. Cl.
CPC .......... *C12N 5/0667* (2013.01); *C12N 2501/21* (2013.01); *A61K 35/12* (2013.01)
USPC .......................................... 424/93.1; 435/377

(58) Field of Classification Search
CPC combination set(s) only.
See application file for complete search history.

(56) References Cited

U.S. PATENT DOCUMENTS 8,067,234 B2 *  11/2011  March et al. .................. 435/325
2006/0018887 A1 *  1/2006  Kadiyala et al. ............. 424/93.7

OTHER PUBLICATIONS

Banas et al., Stem Cells. Oct. 2008;26(10):2705-12. doi: 10.1634/stemcells.2008-0034. Epub Jun. 5, 2008.*
Kroeze, et al., "Chemokine-Mediated Migration of Skin-Derived Stem Cells: Predominant Role for CCL5/RANTES," Journal of Investigative Dermatology, 2009, pp. 1569-1581, vol. 129.

Shang, et al., Wnt3a signaling promotes proliferation, myogenic differentiation, and migration of rat bone marrow mesenchymal stem cells, Acta Pharmacol Sinica, 2007, pp. 1761-1774, vol. 28.
Lamfers, et al., "Homing properties of adipose-derived stem cells to intracerebral glioma and the effects of adenovirus infection," Cancer Letters, 2009, pp. 78-87, vol. 274.
Ponte, et al., "The In Vitro Migration Capacity of Human Bone Marrow Mesenchymal Stem Cells: Comparison of Chemokine and Growth Factor Chemotactic Activities," Stem Cells, 2007, pp. 1737-1745, vol. 25.
Honczarenko, et al., "Human Bone Marrow Stromal Cells Express a Distinct Set of Biologically Functional Chemokine Receptors," Stem Cells, 2006, pp. 1030-1041, vol. 24.
Sordi, et al., "Bone marrow mesenchymal stem cells express a restricted set of functionally active chemokine receptors capable of promoting migration to pancreatic islets," Blood, Jul. 2005, pp. 419-427, vol. 106.
Fiedler, et al., "BMP-2, BMP-4, and PDGF-bb Stimulate Chemotactic Migration of Primary Human Mesenchymal Progenitor Cells," Journal of Cellular Biochemistry, 2002, pp. 305-312, vol. 87.
Forte, et al., "Hepatocyte Growth Factor Effects on Mesenchymal Stem Cells: Proliferation, Migration, and Differentiation," Stem Cells, 2006, pp. 23-33, vol. 24.
Okumura, et al., "Chemotactic and Chemokinetic Activities of stem Cell Factor on Murine Hematopoietic Progenitor Cells," Blood, May 1996, pp. 4100-4108, vol. 87.
Son, et al., "Migration of Bone Marrow and Cord Blood Mesenchymal Stem Cells In Vitro Is Regulated by Stromal-Derived Factor-1-CXCR4 and Hepatocyte Growth Factor-c-met Axes and Involves Matrix Metalloproteinases," Stem Cells, 2006, pp. 1254-1264, vol. 24.
International Search Report, Jul. 1, 2011.
Safford, et al., Stem cell therapy for neurologic disorders: therapeutic potential of adipose-derived stem cells, Current Drug Targets, 2005, pp. 57-62, vol. 6, Abstract.

* cited by examiner

*Primary Examiner* — Daniel C Gamett
(74) *Attorney, Agent, or Firm* — Hulquist, PLLC; Steven J. Hultquist; Mary B. Grant

(57) ABSTRACT

The present invention relates to the ability of adipose tissue-derived adult stem cells to migrate, and more particularly to the novel use of adipose tissue-derived adult stem cells primed with a specific chemokine or growth factor and their specific secretory products, which more effectively migrate to a disease site in vivo. The inventive composition containing either adipose-derived adult stem cells or adipose tissue-derived adult stem cells primed with a specific chemokine or growth factor can be administered by a simple method such as intravenous administration and are able to induce the targeting of the stem cells to a disease site. Thus, the composition is useful as a cell therapeutic agent.

3 Claims, 7 Drawing Sheets

Chemokine receptors expressed in stem cells

Growth factor receptors expressed in stem cells

Growth factor receptors expressed in A549 cells

SEQUENCE LISTING

<160> NUMBER OF SEQ ID NOS: 34

<210> SEQ ID NO 1
<211> LENGTH: 23
<212> TYPE: DNA
<213> ORGANISM: Artificial Sequence

```
<220> FEATURE:
<223> OTHER INFORMATION: Synthetic Construct

<400> SEQUENCE: 1
catcttggct tccatgccag gct                                         23

<210> SEQ ID NO 2
<211> LENGTH: 24
<212> TYPE: DNA
<213> ORGANISM: Artificial Sequence
<220> FEATURE:
<223> OTHER INFORMATION: Synthetic Construct

<400> SEQUENCE: 2
cctccgtcac ttgcacagcc aggt                                        24

<210> SEQ ID NO 3
<211> LENGTH: 24
<212> TYPE: DNA
<213> ORGANISM: Artificial Sequence
<220> FEATURE:
<223> OTHER INFORMATION: Synthetic Construct

<400> SEQUENCE: 3
cctcctgaca atcgatagat acct                                        24

<210> SEQ ID NO 4
<211> LENGTH: 24
<212> TYPE: DNA
<213> ORGANISM: Artificial Sequence
<220> FEATURE:
<223> OTHER INFORMATION: Synthetic Construct

<400> SEQUENCE: 4
gtcacctgcg tggcttggtc cagt                                        24

<210> SEQ ID NO 5
<211> LENGTH: 22
<212> TYPE: DNA
<213> ORGANISM: Artificial Sequence
<220> FEATURE:
<223> OTHER INFORMATION: Synthetic Construct

<400> SEQUENCE: 5
atctccaaga ccagagatag tg                                          22

<210> SEQ ID NO 6
<211> LENGTH: 22
<212> TYPE: DNA
<213> ORGANISM: Artificial Sequence
<220> FEATURE:
<223> OTHER INFORMATION: Synthetic Construct

<400> SEQUENCE: 6
aaatgttgct ctcttaacga at                                          22

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
gaggagttag ccaagatgtg                                             20
```

```
<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
ttcttctggt aacccatgac                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
catcctaatc atccaatgct                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
agctcttttc ttccctctgt                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
ccttaaccct gtgctctatg                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct

<400> SEQUENCE: 12
ctcacctctt caaccttcag                                              20

<210> SEQ ID NO 13
<211> LENGTH: 25
<212> TYPE: DNA
<213> ORGANISM: Artificial Sequence
<220> FEATURE:
<223> OTHER INFORMATION: Synthetic Construct

<400> SEQUENCE: 13
gcatctgcct cacctccacc gtgca                                        25

<210> SEQ ID NO 14
<211> LENGTH: 25
<212> TYPE: DNA
<213> ORGANISM: Artificial Sequence
<220> FEATURE:
<223> OTHER INFORMATION: Synthetic Construct
```

<400> SEQUENCE: 14
gattccgtca tatggcttgg atcca                                          25

<210> SEQ ID NO 15
<211> LENGTH: 25
<212> TYPE: DNA
<213> ORGANISM: Artificial Sequence
<220> FEATURE:
<223> OTHER INFORMATION: Synthetic Construct

<400> SEQUENCE: 15
cctgaccaca gaattggagg ctaca                                          25

<210> SEQ ID NO 16
<211> LENGTH: 24
<212> TYPE: DNA
<213> ORGANISM: Artificial Sequence
<220> FEATURE:
<223> OTHER INFORMATION: Synthetic Construct

<400> SEQUENCE: 16
agttcatgtg taaggtgtac agtg                                           24

<210> SEQ ID NO 17
<211> LENGTH: 25
<212> TYPE: DNA
<213> ORGANISM: Artificial Sequence
<220> FEATURE:
<223> OTHER INFORMATION: Synthetic Construct

<400> SEQUENCE: 17
ccacgtgtgc caacaacatc aacca                                          25

<210> SEQ ID NO 18
<211> LENGTH: 24
<212> TYPE: DNA
<213> ORGANISM: Artificial Sequence
<220> FEATURE:
<223> OTHER INFORMATION: Synthetic Construct

<400> SEQUENCE: 18
tgaagaacga cctaacctgc tgcc                                           24

<210> SEQ ID NO 19
<211> LENGTH: 20
<212> TYPE: DNA
<213> ORGANISM: Artificial Sequence
<220> FEATURE:
<223> OTHER INFORMATION: Synthetic Construct

<400> SEQUENCE: 19
gagaggccat agctgtctgg                                                20

<210> SEQ ID NO 20
<211> LENGTH: 20
<212> TYPE: DNA
<213> ORGANISM: Artificial Sequence
<220> FEATURE:
<223> OTHER INFORMATION: Synthetic Construct

<400> SEQUENCE: 20
gttcctttgt ggcacttggt                                                20

<210> SEQ ID NO 21

<211> LENGTH: 20
<212> TYPE: DNA
<213> ORGANISM: Artificial Sequence
<220> FEATURE:
<223> OTHER INFORMATION: Synthetic Construct

<400> SEQUENCE: 21
gaagctgtca acctgcatga                                        20

<210> SEQ ID NO 22
<211> LENGTH: 20
<212> TYPE: DNA
<213> ORGANISM: Artificial Sequence
<220> FEATURE:
<223> OTHER INFORMATION: Synthetic Construct

<400> SEQUENCE: 22
cttctttagc acggatcagc                                        20

<210> SEQ ID NO 23
<211> LENGTH: 24
<212> TYPE: DNA
<213> ORGANISM: Artificial Sequence
<220> FEATURE:
<223> OTHER INFORMATION: Synthetic Construct

<400> SEQUENCE: 23
gcggctggtg gagccggtga ctga                                   24

<210> SEQ ID NO 24
<211> LENGTH: 25
<212> TYPE: DNA
<213> ORGANISM: Artificial Sequence
<220> FEATURE:
<223> OTHER INFORMATION: Synthetic Construct

<400> SEQUENCE: 24
ctcacttagc tccagcactc ggaca                                  25

<210> SEQ ID NO 25
<211> LENGTH: 24
<212> TYPE: DNA
<213> ORGANISM: Artificial Sequence
<220> FEATURE:
<223> OTHER INFORMATION: Synthetic Construct

<400> SEQUENCE: 25
gtgaacgagg ccgcaagcat gcgt                                   24

<210> SEQ ID NO 26
<211> LENGTH: 25
<212> TYPE: DNA
<213> ORGANISM: Artificial Sequence
<220> FEATURE:
<223> OTHER INFORMATION: Synthetic Construct

<400> SEQUENCE: 26
ctgtggacga acttattggc gttga                                  25

<210> SEQ ID NO 27
<211> LENGTH: 20
<212> TYPE: DNA
<213> ORGANISM: Artificial Sequence
<220> FEATURE:
<223> OTHER INFORMATION: Synthetic Construct

<400> SEQUENCE: 27

```
caggcagtgc agcatgtagt                                               20

<210> SEQ ID NO 28
<211> LENGTH: 20
<212> TYPE: DNA
<213> ORGANISM: Artificial Sequence
<220> FEATURE:
<223> OTHER INFORMATION: Synthetic Construct

<400> SEQUENCE: 28
gatgattccc tcggtcagaa                                               20

<210> SEQ ID NO 29
<211> LENGTH: 26
<212> TYPE: DNA
<213> ORGANISM: Artificial Sequence
<220> FEATURE:
<223> OTHER INFORMATION: Synthetic Construct

<400> SEQUENCE: 29
gctgacacgg tggaactggc tgaact                                        26

<210> SEQ ID NO 30
<211> LENGTH: 27
<212> TYPE: DNA
<213> ORGANISM: Artificial Sequence
<220> FEATURE:
<223> OTHER INFORMATION: Synthetic Construct

<400> SEQUENCE: 30
ctgtatgaat gcggaagatg ctcttga                                       27

<210> SEQ ID NO 31
<211> LENGTH: 27
<212> TYPE: DNA
<213> ORGANISM: Artificial Sequence
<220> FEATURE:
<223> OTHER INFORMATION: Synthetic Construct

<400> SEQUENCE: 31
ggcaacattt ggacacatct cttaggt                                       27

<210> SEQ ID NO 32
<211> LENGTH: 27
<212> TYPE: DNA
<213> ORGANISM: Artificial Sequence
<220> FEATURE:
<223> OTHER INFORMATION: Synthetic Construct

<400> SEQUENCE: 32
cagctcctgt gatgtagagg ctggcca                                       27

<210> SEQ ID NO 33
<211> LENGTH: 21
<212> TYPE: DNA
<213> ORGANISM: Artificial Sequence
<220> FEATURE:
<223> OTHER INFORMATION: Synthetic Construct

<400> SEQUENCE: 33
aatcccatca ccatcttcca g                                             21

<210> SEQ ID NO 34
<211> LENGTH: 21
<212> TYPE: DNA
```

```
<213> ORGANISM: Artificial Sequence
<220> FEATURE:
<223> OTHER INFORMATION: Synthetic Construct

<400> SEQUENCE: 34
aggggccatc cacagtcttc t                                              21
```

METHOD FOR INDUCING MIGRATION OF ADIPOSE-DERIVED ADULT STEM CELLS

CROSS-REFERENCE TO RELATED APPLICATIONS

This application is filed under the provisions of 35 U.S.C. §371 and claims the priority of International Patent Application No. PCT/KR2010/007329 filed on 25 Oct. 2010 entitled "Method for Inducing Migration of Adipose-Derived Adult Stem Cells" in the name of Jeong Chan R A, et al., which claims priority of Korean Patent Application No. 10-2009-0101117 filed on 23 Oct. 2009, both of which are hereby incorporated by reference herein in their entirety.

TECHNICAL FIELD

The present invention relates to the ability of adipose tissue-derived adult stem cells to migrate, and more particularly to the novel use of adipose tissue-derived adult stem cells and their specific secretory products, which have the ability to migrate to a disease site in which chemokines or growth factors are expressed, and to a method capable of more effectively enhancing the function of the receptors for chemokines or growth factors.

BACKGROUND ART

Stem cells refer to cells having not only self-replicating ability but also the ability to differentiate into at least two types of cells, and can be divided into totipotent stem cells, pluripotent stem cells, and multipotent stem cells.

Totipotent stem cells are cells having totipotent properties capable of developing into one perfect individual, and these properties are possessed by cells up to the 8-cell stage after the fertilization of an oocyte and a sperm. When these cells are isolated and transplanted into the uterus, they can develop into one perfect individual. Pluripotent stem cells, which are cells capable of developing into various cells and tissues derived from the ectodermal, mesodermal and endodermal layers, are derived from an inner cell mass located inside of blastocysts generated 4-5 days after fertilization. These cells are called "embryonic stem cells" and can differentiate into various other tissue cells but not form new living organisms. Multipotent stem cells, which are stem cells capable of differentiating into only cells specific to tissues and organs containing these cells, are involved not only in the growth and development of various tissues and organs in the fetal, neonatal and adult periods but also in the maintenance of homeostasis of adult tissue and the function of inducing regeneration upon tissue damage. Tissue-specific multipotent cells are collectively called "adult stem cells".

Adult stem cells are obtained by taking cells from various human organs and developing the cells into stem cells and are characterized in that they differentiate into only specific tissues. However, recently, experiments for differentiating adult stem cells into various tissues, including liver cells, were dramatically successful, which comes into spotlight.

Efforts have been made in the field of regenerative medicine for regenerating biological tissues and organs and recovering their functions that were lost due to illness or accident and the like by using cells. Methods which are frequently used in this field of regenerative medicine comprise the steps of: collecting stem cells, blood-derived mononuclear cells or marrow-derived mononuclear cells from a patient; inducing the proliferation and/or differentiation of the cells by tube culture; and introducing the selected undifferentiated (stem cells and/or progenitor cells) and/or differentiated cells into the patient's body by transplantation. Accordingly, existing classical methods for treating diseases by medication or surgery are expected to be replaced with cell/tissue replacement therapy which replaces a damage cell, tissue or organ with healthy one, and thus the utility of stem cells will further increase.

Thus, the various functions of stem cells are currently being studied. Particularly, various studies on the efficient isolation of stem cells, the maintenance and proliferation of stem cells in an undifferentiated state and the differentiation of stem cells into tissue cells are in progress. There have been a number of reports on the migration of marrow-derived stem cells induced by treatment with chemokines (Adriana Lopez Ponte et al., *Stem Cells*, 25:1737-1745, 2007; Marek Honczarenko et al., *Stem Cells*, 24:1031-1041, 2006; Sordi V et al., *Blood*, 106:419-427, 2005; Fiedler J et al., *J Cell Biochem*, 87:305-312, 2002; Forte G et al., *Stem Cells*, 24:23-33, 2006; Wright D E et al., *Blood*, 87:4100-4108, 1996; Son B R et al., *Stem Cells*, 24:1254-1264, 2006), but there has been no report on the migration of adipose stem cells.

Accordingly, the present inventors have found that adipose mesenchymal stem cells have the ability to migrate and that the migration of adipose mesenchymal stem cells by a specific chemokine or growth factor is remarkably induced when the stem cells are primed with various chemokines or growth factors. Based on this finding, the present inventors have found a method capable of enhancing the ability of adipose-derived mesenchymal stem cells to express the receptors for chemokines or growth factors, thereby completing the present invention.

DISCLOSURE OF INVENTION

It is an object of the present invention to provide a composition for inducing the migration of adipose stem cells, the composition containing as an active ingredient one or more of adipose tissue-derived adult stem cells and their secretory products.

Another object of the present invention is to provide a method for inducing the migration of adipose tissue-derived adult stem cells to a disease site.

The present invention is directed to the use and function of adipose tissue-derived adult stem cells, which express the receptors for chemokines or growth factors, or secretory products from the stem cells. To achieve the above objects, the present invention provides a composition for inducing the migration of adipose stem cells, the composition containing, as an active ingredient, adipose-derived adult stem cells and/or their secretory product.

Examples of the secretory product of the adipose-derived adult stem cell in the composition of the present invention include the receptors of Rantes, MCP-1 (monocyte chemoattractant protein-1), MIP-3β (monocyte inflammatory protein-3β), SDF-1α (stromal cell-derived factor-1α), BCA-1 (B cell attracting chemokine-1), CXCL16 (chemokine C-X-C motif ligand 16), EGF (endothelial growth factor), b-FGF (basic fibroblast growth factor), HGF (hepatocyte growth factor), TGF-β1 (transforming growth factor beta 1), IGF-1 (insulin-like growth factor 1), PDGF-AB (platelet derived growth factor AB), TNF-α (tumor necrosis factor-α), adiponectin, leptin, and procollagen. Preferably, the secretory product may be adiponectin and/or leptin.

The adipose tissue-derived adult stem cells and/or their secretory products may be used as a broth of human adipose tissue-derived adult stem cells, obtained by culturing human adipose tissue-derived adult stem cells in a medium containing certain components, harvesting the culture medium, and removing cell debris from the culture medium.

In addition, the composition may further contain FBS. Preferably, the composition may contain about 30% FBS.

The adipose-derived adult stem cells and their secretory products express the receptors for one or more chemokines or growth factors selected from the group consisting of Rantes, MCP-1 (monocyte chemoattractant protein-1), MIP-3β (monocyte inflammatory protein-3M, SDF-1α (stromal cell-derived factor-1α), BCA-1 (B-cell attracting chemokine-1), CXCL16 (chemokine C-X-C motif ligand 16), EGF (endothelial growth factor), b-FGF (basic fibroblast growth factor), HGF (hepatocyte growth factor), TGF-β1 (transforming growth factor beta 1), IGF-1 (insulin-like growth factor 1), PDGF-AB (platelet derived growth factor AB), and TNF-α (tumor necrosis factor-α), and migrate in response to such chemokines or growth factors.

In addition, the adipose-derived adult stem cells in the composition of the present invention may preferably be derived from a mammal, more preferably a human. For example, the adipose-derived adult stem cells may be human adipose tissue-derived mesenchymal stem cells (AdMSCs).

Particularly, the adipose tissue-derived adult stem cells that are used in the present invention are preferably primed with a cocktail containing a chemokine or a growth factor.

Preferably, the cocktail may contain one or more factors selected from the group consisting of Rantes, MCP-1 (monocyte chemoattractant protein-1), MIP-3β (monocyte inflammatory protein-3β), SDF-1α (stromal cell-derived factor-1α), BCA-1 (B-cell attracting chemokine-1), CXCL16 (chemokine C-X-C motif ligand 16), EGF (endothelial growth factor), b-FGF (basic fibroblast growth factor), HGF (hepatocyte growth factor), TGF-β1 (transforming growth factor beta 1), IGF-1 (insulin-like growth factor 1), PDGF-AB (platelet derived growth factor AB), and TNF-α (tumor necrosis factor-α). Particularly, the cocktail may more preferably contain one or more factors selected from the group consisting of Rantes, SDF-1α (stromal cell-derived factor-1α), HGF (hepatocyte growth factor), TNF-α (tumor necrosis factor-α), PDGF-AB (platelet derived growth factor AB), and TGF-β1 (transforming growth factor beta 1).

The human adult stem cells are preferably contained in an amount of about $1\times10^7$ cells to $1\times10^{10}$ cells, and more preferably about $1\times10^8$ cells to $1\times10^9$ cells.

The present invention also provides a method for inducing the migration of adipose tissue-derived adult stem cells, the method comprising the steps of:

(a) priming adipose tissue-derived adult stem cells with a cocktail containing a chemokine or a growth factor; and (b) administering a composition containing the primed adipose tissue-derived adult stem cells and their secretory products into an in vivo site which is not in direct contact with a disease site. In this method, the composition is most preferably administered intravenously.

BRIEF DESCRIPTION OF THE DRAWINGS

In FIG. 7A, lane 1: CCR1 (380 bp), lane 2: CCR2 (474 bp), lane 3: CCR7 (461 bp), lane 4: CXCR4 (489 bp), lane 5: CXCR5 (494 bp), lane 6: CXCR6 (517 bp), and lane 7: GAPDH (362 bp). In FIG. 7B, M: Marker, lane 1: EGFR (419 bp), lane 2: TGFBR2 (498 bp), lane 3: PDGFRA (187 bp), lane 4: PDGFRB (508 bp), lane 5: IGF1R (299 bp), lane 6: c-MET (201 bp), lane 7: TNFRSF1A (218 bp), lane 8: FGFR1 (250 bp), and lane 9: GAPDH (362 bp).

In FIG. 9, lane 1: ADIPOR1 (337 bp), lane 2: ADIPOR2 (538 bp), lane 3: GAPDH (362 bp).

BEST MODE FOR CARRYING OUT THE INVENTION

Figure 1:
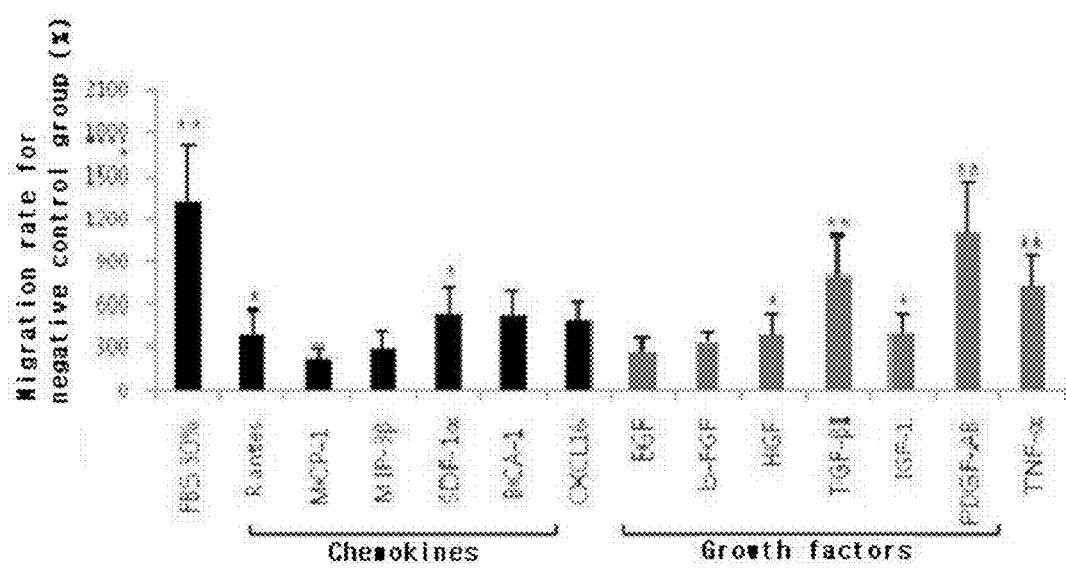
FIG. 1 is a graphic diagram showing the results of inducing the migration of adipose tissue-derived multipotent mesenchymal stem cells by various chemikines or growth factors.

Unless defined otherwise, all technical and scientific terms used herein have the same meaning as commonly understood by one of ordinary skill in the art to which the invention pertains. Generally, the nomenclature used herein and the experiment methods which will be described later are those well known and commonly employed in the art.

Stem cells refer to cells having not only self-replicating ability but also the ability to differentiate into at least two types of cells.

Adult stem cells are stem cells that appear either in the stage in which each organ of an embryo is formed after the developmental process or in the adult stage. It is known that adult stem cells are multipotent and capable of differentiating into tissue- and organ-specific cells. Such multipotent stem cells, which are stem cells capable of differentiating into cells specific to tissues and organs containing these cells, are involved not only in the growth and development of various tissues and organs in the fetal, neonatal and adult periods but also in the maintenance of homeostasis of adult tissue and the function of inducing regeneration upon tissue damage.

In the present invention, adult stem cells derived from adipose tissue or epithelial tissue such as a hair follicle or an amnion may be used. Preferably, human adipose tissue-derived adult stem cells are used. Mesenchymal stem cells (MSCs) may be used. Particularly, human adipose tissue-derived mesenchymal stem cells (AdMSCs) may be used.

Said adipose tissue or epithelial tissue is preferably derived from a mammal, more preferably a human. In one examples of the present invention, human adipose tissue-derived mesenchymal stem cells (AdMSCs) were used.

As used herein, "adipose tissue-derived adult stem cells" or "adipose tissue-derived mesenchymal stem cells" are undifferentiated adult stem cells isolated from adipose tissue and are also referred to herein as "adipose stem cells". These cells can be obtained according to any conventional method known in the art.

The adipose stem cells can be obtained using any conventional medium known in the art to be suitable for stem cell culture. For example, DMEM (Dulbecco's modified Eagle medium) is used in the present invention.

The medium for culturing adipose stem cells may be supplemented with additives that promote the proliferation of the undifferentiated phenotype of the adipose stem cells while inhibiting the differentiation of the cells. Also, the medium may generally contain a neutral buffer (such as phosphate and/or high concentration bicarbonate) in isotonic solution; a protein nutrient (e.g., serum such as FBS, serum replacement, albumin, or essential and non-essential amino acids such as glutamine). Furthermore, it may contain lipids (fatty acids, cholesterol, an HDL or LDL extract of serum) and other ingredients found in most stock media of this kind (such as insulin or transferrin, nucleosides or nucleotides, pyruvate, a sugar source such as glucose, selenium in any ionized form or salt, a glucocorticoid such as hydrocortisone and/or a reducing agent such as β-mercaptoethanol).

In addition, with a view to protecting cells from adhering to each other, adhering to a vessel wall, or forming clusters that are too big, it may be beneficial for the medium to include an anti-clumping agent, such as those sold by Invitrogen (Cat #0010057AE).

Among them, one or more of the following additional additives may advantageously be used:

stem cell factor (SCF, Steel factor), other ligands or antibodies that dimerize c-kit, and other activators of the same signal transduction pathway ligands for other tyrosine kinase related receptors, such as the receptor for platelet-derived growth factor (PDGF), macrophage colony-stimulating factor, Flt-3 ligand and vascular endothelial growth factor (VEGF)

factors that elevate cyclic AMP levels, such as forskolin factors that induce gp130, such as LIF or Oncostatin-M hematopoietic growth factors, such as thrombopoietin (TPO)

transforming growth factors, such as TGFβ1 other growth factors, such as epidermal growth factor (EGF)

neurotrophins, such as CNTF

N-acetyl-L-cysteine (NAC)

hydrocortisone ascrobic acid

Particularly, a medium which is used to culture adipose stem cells in one embodiment of the present invention preferably contains NAC, ascrobic acid, calcium, insulin, and hydrocortisone. More preferably, it contains FBS, NAC, ascrobic acid, calcium, rEGF, insulin, and hydrocortisone.

The composition of the present invention may contain, as an active ingredient, a secretory product from the adipose tissue-derived mesenchymal stem cells.

Examples of this secretory product include a variety of cytokines, amino acids, growth factors and the like. Specific examples of the secretory product that may be contained in the composition of the present invention include TGF, bFGF, IGF-1, KGF, HGF, fibronectin, VEGF, adiponectin, leptin and procollagen, as well as their receptors. Among such secretory products from the adipose-derived adult stem cells, adiponectin or leptin is derived specifically from adipose tissue and greatly contributes to the induction of cell migration.

The human adult stem cells and/or their secretory products may be used as a broth of human adipose tissue-derived adult stem cells, obtained by culturing human adipose tissue-derived adult stem cells in a medium containing certain components, harvesting the culture medium and removing cell debris from the culture medium. Alternatively, extracts from the culture broth may be used alone or in combination.

In other words, the composition of the present invention may be either a composition containing adipose-derived adult stem cells and their secretory products and medium components, or a composition containing the cell secretory products and the medium components, or a composition containing the cell secretory products alone or in combination with adult stem cells, or a composition containing only adipose-derived adult stem cells that produce secretory products in vivo.

In one aspect, the present invention is directed to the use of adipose tissue-derived adult stem cells and/or their secretory products for inducing the migration of stem cells. More specifically, the present invention is based on a finding that adipose tissue-derived adult stem cells and their specific secretory products show the function of a chemokine or growth factor receptor, which are expressed in a disease site.

As used herein, the phrase "show(s) the function of a chemokine or growth factor receptor" refers to the case in which adipose tissue-derived adult stem cells express on the cell surface a receptor that binds specifically to a specific chemokine or growth factor, or in which a secretory product from these cells is the receptor or includes the receptor. In other words, it means that adipose stem cells have the capability to react with a specific chemokine or growth factor.

The growth factors refer to a group of polypeptides that promote the division, growth and differentiation of various cells, and they are known to be involved in cell signaling. The growth factors are classified into families according to structural similarity and act on target cells by mechanisms such as autocrine, palacrine, endocrine and the like. The growth factor receptors generally have tyrosine kinase activity in the intracellular region, and when they bind to ligand receptors, the growth factor receptors themselves or the tyrosine residues of intracellular proteins are phosphorylated and cell proliferation or differentiation occurs.

The chemokines constitute a family of small cytokines which are produced in inflammation and regulate leukocyte recruitment. Such chemokines are capable of selectively inducing chemotaxis of the formed elements of the blood (other than red blood cells), including leukocytes such as neutrophils, monocytes, macrophages, eosinophils, basophils, mast cells, and lymphocytes, such as T cells and B cells. In addition to stimulating chemotaxis, other changes can be selectively induced by chemokines in responsive cells, including changes in cell shape, transient rises in the concentration of intracellular free calcium ions ($Ca^{2+}$), granule exocytosis, integration upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

In general, chemokine/receptor interactions tend to be promiscuous in that one chemokine can bind to many chemokine receptors and conversely a single chemokine receptor can interact with several chemokines. There are many aspects of chemokine receptor signaling and selectivity for ligands that were not previously understood.

Based on a new finding that adipose-derived adult stem cells and their secretory products show the function of such chemokine receptors, the present invention aims to use the function of adipose-derived adult stem cells that migrate to a site of infection or inflammation (i.e., a disease site) in response to a specific chemokine that is expressed in the disease site (this migration also referred to as "targeted migration"). In the present invention, responses not only for chemokines, but also for specific growth factors, are also considered. Specifically, the adipose-derived adult stem cells are excellent in the response to chemokines or growth factors selected from the group consisting of Rantes, MCP-1 (monocyte chemoattractant protein-1), MIP-3β (monocyte inflammatory protein-3β), SDF-1α (stromal cell-derived factor-1α), BCA-1 (B-cell attracting chemokine-1), CXCL16 (chemokine C-X-C motif ligand 16), EGF (endothelial growth factor), b-FGF (basic fibroblast growth factor), HGF (hepatocyte growth factor), TGF-β1 (transforming growth factor beta 1), IGF-1 (insulin-like growth factor 1), PDGF-AB (platelet derived growth factor AB), and TNF-α (tumor necrosis factor-α).

In order to increase the ability of cells to migrate by the interaction of the chemokines or growth factors and their receptors, the composition of the present invention may further contain FBS. Preferably, the composition contains about 30% FBS. It is to be understood that, even when the composition contains no FBS, it can use FBS present in the body when administered into the body.

Meanwhile, in order to increase the expression level or the reaction of the adipose tissue-derived adult stem cells and/or the receptor of the secretory product of the adipose tissue-derived adult stem cells, the adipose tissue-derived adult stem cells are preferably primed with a cocktail containing a chemokine or a growth factor.

Particularly, the cocktail may preferably contain one or more factors selected from the group consisting of Rantes, MCP-1 (monocyte chemoattractant protein-1), MIP-3β (monocyte inflammatory protein-3β), SDF-1α (stromal cell-derived factor-1α), BCA-1 (B-cell attracting chemokine-1), CXCL16 (chemokine C-X-C motif ligand 16), EGF (endothelial growth factor), b-FGF (basic fibroblast growth factor), HGF (hepatocyte growth factor), TGF-β1 (transforming growth factor beta 1), IGF-1 (insulin-like growth factor 1), PDGF-AB (platelet derived growth factor AB), and TNF-α (tumor necrosis factor-α). The cocktail may more preferably contain one or more factors selected from the group consisting of Rantes, SDF-1α (stromal cell-derived factor-1α), HGF (hepatocyte growth factor), TNF-α (tumor necrosis factor-α), PDGF-AB (platelet derived growth factor AB), and TGF-β1 (transforming growth factor beta 1).

As can be seen in Example 5 of the present invention, in the case of adipose tissue-derived adult stem cells primed with a specific chemokine or growth factor and/or the secretory product of the cells, the migration of cells in response to the chemokine or growth factor significantly increases.

Thus, in another aspect, the present invention is directed to a method for inducing the migration of adipose tissue-derived adult stem cells, the method comprising the steps of:
(a) priming adipose tissue-derived adult stem cells with a cocktail containing a chemokine or a growth factor; and
(b) administering a composition containing the primed adipose tissue-derived adult stem cells and their secretory products into an in vivo site which is not in direct contact with a disease site.

In the method of the present invention, step (a) of priming the adult stem cells with the cocktail containing the chemokine or the growth factor may be performed by culturing the adult stem cells in a medium containing the chemokine or the growth factor. The priming of the adult stem cells is carried out for about 20-60 hours, preferably about 20-50 hours. In one embodiment of the present invention, the priming of the adult stem cells is carried out for 24 hours. In addition, the priming of the adipose stem cells with the cocktail is carried out before, during or after culture of the adipose stem cells. Preferably, it is carried out after culture of the adipose stem cells.

The cocktail may preferably contain one or more factors selected from the group consisting of Rantes, MCP-1 (monocyte chemoattractant protein-1), MIP-3β (monocyte inflammatory protein-3β), SDF-1α (stromal cell-derived factor-1α), BCA-1 (B-cell attracting chemokine-1), CXCL16 (chemokine C-X-C motif ligand 16), EGF (endothelial growth factor), b-FGF (basic fibroblast growth factor), HGF (hepatocyte growth factor), TGF-β1 (transforming growth factor beta 1), IGF-1 (insulin-like growth factor 1), PDGF-AB (platelet derived growth factor AB), and TNF-α (tumor necrosis factor-α). More preferably, the cocktail may contain one or more factors selected from the group consisting of Rantes, SDF-1α (stromal cell-derived factor-1α), HGF (hepatocyte growth factor), TNF-α (tumor necrosis factor-α), PDGF-AB (platelet derived growth factor AB), and TGF-β1 (transforming growth factor beta 1).

In addition, the composition containing the primed adipose-derived adult stem cells and/or their secretory products, which is used in step (b), may be either a composition containing all the primed adipose stem cells, the secretory products and the medium, or a composition containing the secretory products and the medium without the primed adipose stem cells, or a composition containing the primed adipose stem cells without the secretory products and the medium. Thus, the primed adipose stem cells, the secretory products and the medium may be used in various ways, but is particularly not limited.

Further, as used herein, the phrase "administering the composition into an in vivo site which is not in direct contact with a disease site" means positioning stem cells in a subject by methods or routes of inducing at least partial localization of stem cells in sites other than the disease site, excluding a method of transplanting stem cells into the disease site. The composition of the present invention can be administered to a subject by any suitable route such that it is delivered to a desired position of the subject in which some the components of cells are still viable. As used herein, the term "administering" can be used interchangeably with "introducing", "delivering", "positioning" or the like. For clinical administration, the composition of the present invention can be administered parenterally, for example, by intramuscular or intravenous injection. Most preferably, the composition of the present invention is administered by intravenous injection.

Thus, the present invention is directed to a method for inducing the migration of adipose tissue-derived adult stem cells, the method comprising intravenously administering a composition containing adipose tissue-derived adult stem cells primed with a chemokine or a growth factor and/or their secretory product.

In still another aspect, the present invention is directed to a method of inducing the targeted migration of adipose tissue-derived adult stem cells to allow the cells to reach a disease site, thereby treating the disease site. Thus, the present invention is directed to a cell therapeutic agent containing, as active ingredients, adipose tissue-derived adult stem cells and their secretory products and a method of using the cell therapeutic agent to treat a disease site.

Unless otherwise indicated, the term "treating", as used herein, means reversing, alleviating, inhibiting the progress of, or preventing the disorder or condition to which such term applies, or one or more symptoms of such disorder or condition. The term "treatment", as used herein, refers to the act of treating as "treating" is defined immediately above. Thus, as used herein, "treating" or "treatment" of a disease in a mammal includes one or more of:

(1) inhibiting growth of the disease, i.e., arresting its development;

(2) preventing spread of the disease, i.e., preventing metastases;

(3) relieving the disease, i.e., causing regression of the cancer;

(4) preventing recurrence of the disease; and (5) palliating symptoms of the disease.

In order to treat a disease site by allowing stem cells to migrate to the disease site, the composition of the present invention is administered in a pharmaceutically effective amount.

As used herein, the term "therapeutically effective amount" means that an amount of the compound being administered alleviates to some extent one or more of the symptoms of the disease being treated. Therefore, the therapeutically effective amount refers to an amount that has the effect of: (1) reversing the rate of progress of a disease; (2) inhibiting the progress of the disease to some extent; or (3) relieving (preferably eliminating) one or more symptoms associated with the disease to some extent.

The composition (cell therapeutic agent) of the present invention may be clinically administered parenterally, such as intramuscularly or intravenously. Most preferably, the composition of the present invention is administered by intravenous injection.

For injection, the composition of the present invention may preferably be formulated with a pharmacologically acceptable buffer, such as Hank's solution, Ringer's solution or physiological saline buffer. For transmucous administration, non-invasive agents suitable for a barrier through which the composition is to be passed are used in formulation. Such non-invasive agents are generally known in the art.

Formulations for parenteral administration include sterilized aqueous solutions, non-aqueous solvents, suspending agents, emulsifying agents. Suspending agents and emulsifying agents that may be used in the present invention include vegetable oils, such as propylene glycol, polyethylene glycol and olive oil, and injectable ester such as ethyl oleate.

For humans, the cell therapeutic agent of the present invention may conventionally be administered once or several times at a dose of $10^4$-$10^{10}$ cells/body, and preferably $10^6$-$10^8$ cells/body. Particularly, the composition of the present invention preferably contains adult stem cells at a concentration of $1 \times 10^8$ cells/100 µl to $1 \times 10^9$ cells/100 µl.

However, it is to be understood that the actual dose of the active ingredient of the composition should be determined according to various related factors, including the disease to be treated, the route of administration, the patient's age, sex and weight, and the severity of disease. Thus, the above dose does not limit the scope of the present invention in any way.

EXAMPLES

Hereinafter, the present invention will be described in further detail with reference to examples. It will be obvious to those skilled in the art that these examples are illustrative purposes only and are not to be construed to limit the scope of the present invention.

The sources of the media and reagents used in Examples below are shown in Table 1 below.

TABLE 1

| Items | Brands | |
|---|---|---|
| Ascorbic acid | Sigma | USA |
| $CaCl_2$ | Sigma | USA |
| Collagenase type I | Gibco | USA |
| DMEM | Gibco | USA |
| DPBS | Welgene | Korea |
| EGF | Gibco | USA |
| FBS | Gibco | USA |
| Hydrocortisone | Sigma | USA |
| Insulin | Gibco | USA |
| K-SFM | Gibco | USA |
| NAC | Sigma | USA |

Example 1

Isolation of Mesenchymal Stem Cells Derived From Human Adipose Tissue

Human adipose tissue was isolated from abdominal fat by liposuction and washed with PBS. The isolated tissue was cut finely and then digested in DMEM media supplemented with collagenase type 1 (1 mg/ml) at 37° C. for 2 hours. After washing with PBS, the digested tissue was centrifuged at 1000 rpm for 5 minutes. The supernatant was suctioned off, and the pellets remaining at the bottom were washed with PBS and then centrifuged at 1000 rpm for 5 minutes. The resulting cells were filtered through a 100-µm mesh filter to remove the debris, after which the cells were washed with PBS and then cultured overnight in DMEM (10% FBS, 2 mM NAC, 0.2 mM ascorbic acid).

Then, non-adherent cells were removed by washing with PBS, and the remaining cells were subcultured while the medium was replaced with Keratinocyte-SFM medium (containing 5% FBS, 2 mM NAC, 0.2 mM ascorbic acid, 0.09 mM calcium, 5 ng/ml rEGF, 5 µg/ml insulin, and 74 ng/ml hydrocortisone) at 2-day intervals, thereby isolating adipose tissue-derived multipotent mesenchymal stem cells.

Example 2

Induction of Migration of Adipose Stem Cells 2-1: Induction of Cell Migration by the Chemokines or Growth Factors Shown in Table 2

The adipose tissue-derived multipotent mesenchymal stem cells isolated in Example 1 were seeded into each well at a concentration of $2 \times 10^4$ cells/200 µl and were induced to migrate by the chemokines or growth factors shown in Table 2 below. As a positive control group, 30% FBS was used.

TABLE 2

| FBS 30% | BCA-1 | TGF-β1 |
|---|---|---|
| Rantes | CXCL16 | IGF-1 |
| MCP-1 | EGF | PDGF-AB |
| MIP-3β | b-FGF | TNF-α |
| SDF-1α | HGF | |

FIG. 1 shows the results of induction of the cell migration. As a negative control group, cells induced to migrate by media were used, and as a positive control group, and cells induced to migrate by 30% FBS were used. The results of induction of the cell migration were calculated as a percentage relative to the negative control group being taken as 100%, and the results of the calculation are graphically shown in FIG. 1. As can be seen in FIG. 1, the adipose tissue-derived mesenchymal stem cells (AdMSCs) actively migrated in response to stimulation with chemokines or growth factors in the same manner as stimulation with 30% FBS. Particularly, the cells were actively induced to migrate in response to Rantes, SDF-1α, HGF, TGF-β1, IGF-1, PDGF-AB, or TNF-α.

2-2: Imaging of Cells Induced to Migrate by Other Chemokines or Growth Factors

Figure 2:
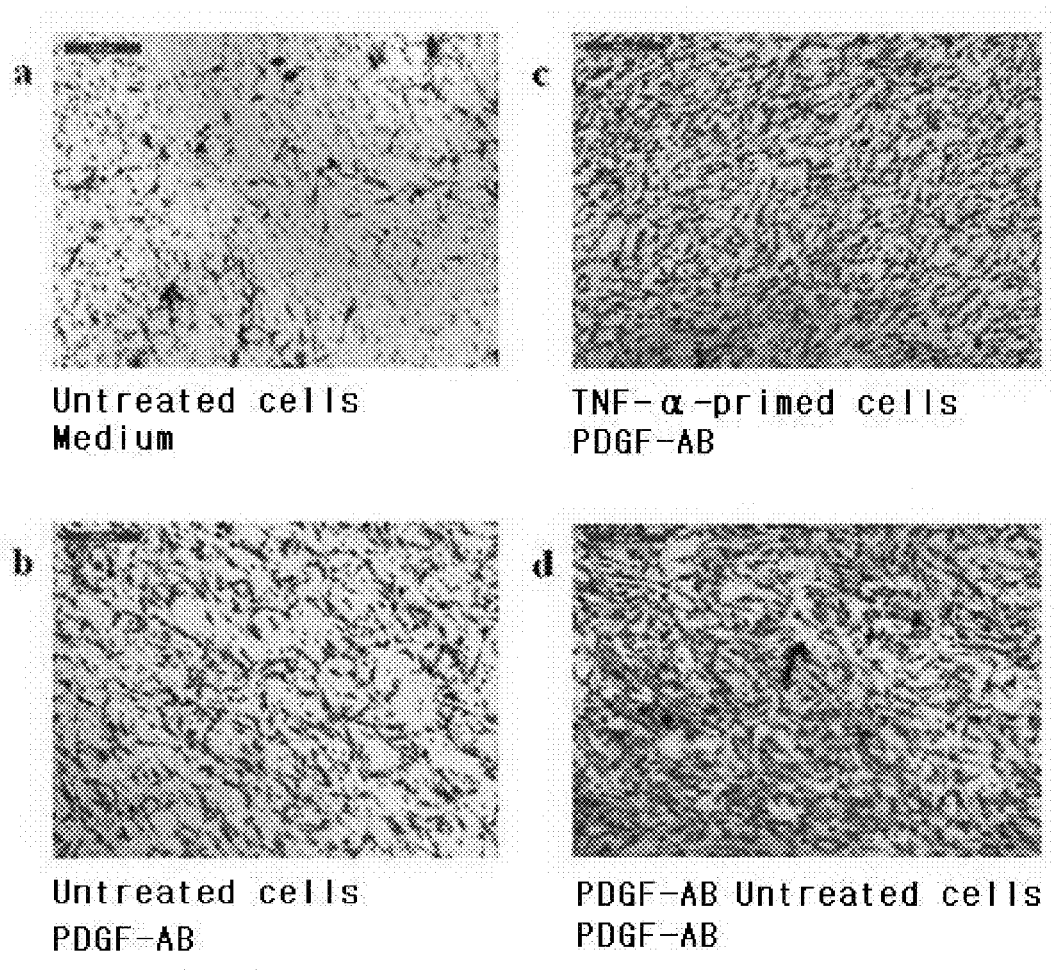
FIG. 2 is a set of micrographs of adipose tissue-derived multipotent mesenchymal stem cells, taken after inducing the migration of the cells.

The adipose tissue-derived multipotent mesenchymal stem cells isolated in Example 1 were primed with FBS-free media (FIG. 2A), TNF-α (FIGS. 2B and 2C) or chemotactic factor (FIG. 2D) for 24 hours and cultured. Then, the cells were isolated by treatment with 0.25% trypsin/1 mM EDTA, after which these cells were washed with PBS and collected by centrifugation at 1,500 rpm for 5 minutes.

Then, transwell inserts (Costar, 3422) were coated with 0.1% gelatin (Sigma-Aldrich) for 2 hours and placed in a 24-well plate containing a medium. The collected adipose stem cells were seeded into each insert at a concentration of $2\times10^4$ cells/200 μl and cultured in a 5% $CO_2$ incubator at 37° C. for 2 hours. Then, the seeded insert was transferred into a 24-well plate containing each of media, chemokines and growth factors at a concentration of 100 ng/ml. Then, the cells were cultured in a 5% $CO_2$ incubator at 37° C. for 24 hours. Then, non-migrated adipose stem cells present in the upper portion of the insert were removed with a cotton swab, and the remaining cells were washed and then immobilized with 70% methanol for 1 hour.

Then, the cells were stained with a 0.5% crystal violet solution for 1 hour. Then, the cells were washed and then imaged under a microscope at ×100 magnification.

As a result, as can be seen in FIGS. 2A to 2D, the rate of migration of the primed adipose stem cells (FIGS. 2C and 2D) were higher than that of the non-primed adipose stem cells (FIGS. 2A and 2B), indicating that the primed cells were dense.

Example 3

Migration of Adipose Stem Cells Primed with Chemokines or Growth Factors

The adipose tissue-derived multipotent mesenchymal stem cells isolated in Example 1 were primed with the chemokines or growth factors shown in Table 3 below for 24 hours. The primed cells were seeded into each well at a concentration of $2\times10^4$ cells/200 μl and were induced to migrate by 10% FBS in order to observe the difference from the induction of cell migration by 30% FBS. Meanwhile, non-primed adipose-derived multipotent mesenchymal stem cells (untreated cells) were used as a negative control group.

TABLE 3

| | |
|---|---|
| Rantes | TNF-α |
| SDF-1α | PDGF-AB |
| HGF | TGF-β1 |

Figure 3:
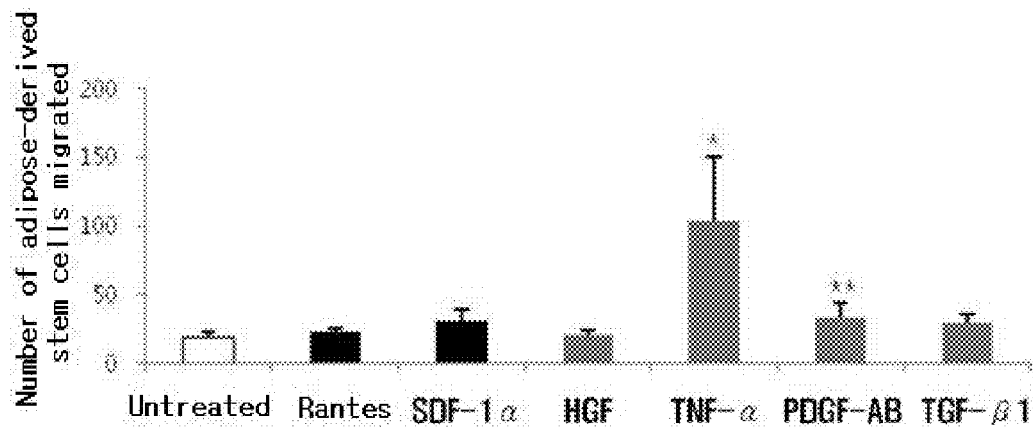
FIG. 3 is a graphic diagram showing the results of inducing the migration of adipose tissue-derived multipotent mesenchymal stem cells, primed with various chemokines or growth factors, by 10% FBS.

FIG. 3 shows the results of induction of the cell migration. From the number of migrated cells as shown in FIG. 3, it could be seen that, among the adipose tissue-derived mesenchymal stem cells (AdMSCs) primed with various chemokines or growth factors, those primed with PDGF-AB or TNF-α were actively induced to migrate by 10% FBS. Particularly, the cells primed with TNF-α were remarkably actively induced to migrate.

Example 4

Migration of Adipose Stem Cells Primed with TNF-α

With reference to the test results obtained in Example 3, the adipose tissue-derived multipotent mesenchymal stem cells isolated in Example 1 were primed with TNF-α for 24 hours. The primed cells were seeded into each well at a concentration of $2\times10^4$ cells/200 μl and induced to migrate by the various chemokines or growth factors shown in Table 4 below.

TABLE 4

| | | |
|---|---|---|
| FBS (none) | BCA-1 | TGF-β1 |
| Rantes | CXCL16 | IGF-1 |
| MCP-1 | EGF | PDGF-AB |
| MIP-3β | b-FGF | TNF-α |
| SDF-1α | HGF | |

Figure 4:
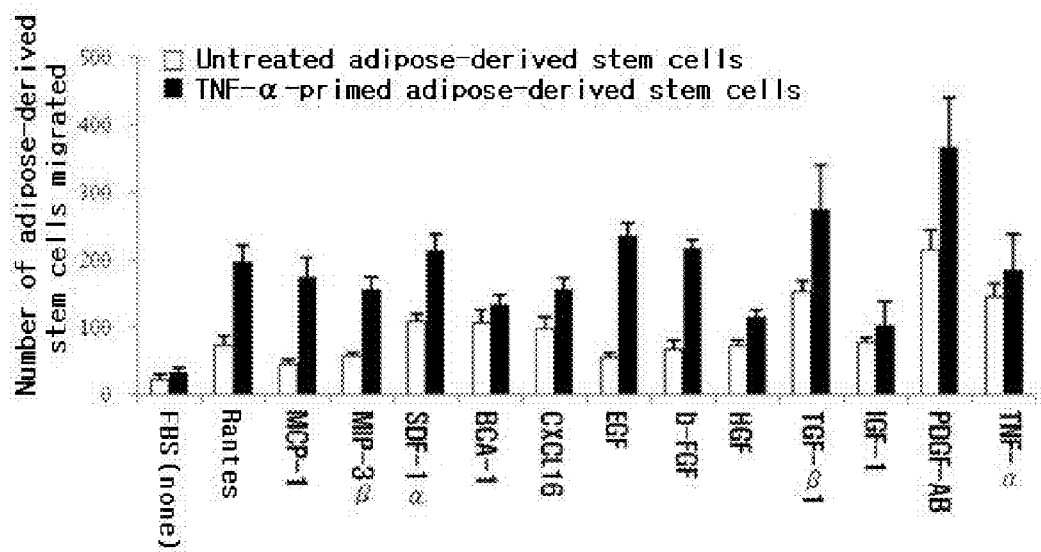
FIG. 4 is a graphic diagram showing the results of inducing the migration of adipose tissue-derived multipotent mesenchymal stem cells, primed with TNF-α, by various chemokines or growth factors.

FIG. 4 shows the results of induction of the cell migration. As can be seen in FIG. 4, the adipose tissue-derived mesenchymal stem cells (AdMSCs) primed with TNF-α were actively induced to migrate by Rantes, SDF-1α, EGF, β-FGF, TGF-β1, PDGF-AB and the like. Particularly, when the results in FIG. 4 were compared with the results in FIG. 1 showing the results of Example 1, the effect of priming with TNF-α could be demonstrated. Specifically, it could be seen that when the cells were primed with TNF-α, the migration of the cells became active.

Example 5

Priming of Adipose Stem Cells with Various Chemokines or Growth Factors and the Ability of Chemokines or Growth Factors to Induce Cell Migration The adipose tissue-derived multipotent mesenchymal stem cells isolated in Example 1 were primed with the chemokines or growth factors shown in Table 5 below for about 24 hours. The primed cells were seeded into each well at a concentration of $2\times10^4$ cells/200 μl and were induced to migrate using the same chemokines or growth factors used in the priming.

TABLE 5

| | | |
|---|---|---|
| FBS 30% | BCA-1 | TGF-β1 |
| Rantes | CXCL16 | IGF-1 |
| MCP-1 | EGF | PDGF-AB |
| MIP-3β | b-FGF | TNF-α |
| SDF-1α | HGF | |

Figure 5:
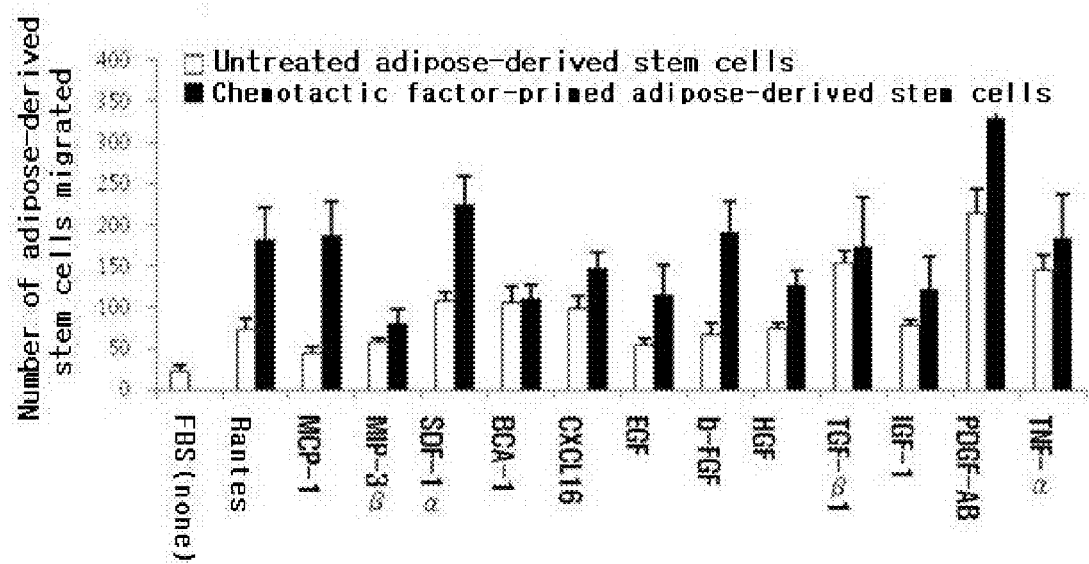
FIG. 5 is a graphic diagram showing the results of inducing the migration of adipose tissue-derived multipotent mesenchymal stem cells, primed with various chemokines or growth factors, by the same chemokines or growth factors used to prime the cells.

FIG. 5 shows the results of induction of the cell migration. In FIG. 5, the white bar graphs indicate non-primed cells, and the black bar graphs indicate the number of cells that migrated as a result of priming with the chemokines or growth factors. As can be seen in FIG. 5, the migration of the adipose stem cells primed with Rantes, MIP-3β, SDF-1α, BCA-1, CXCL16, EGF, PDGF-AB or the like was improved compared to that of the non-primed adipose stem cells. Particularly, the ability of the cells to migrate was significantly increased when primed with Rantes, SDF-1α, BCA-1, CXCL16 or PDGF-AB.

Example 6

Expression of the Receptors for Chemokines or Growth Factors in Adipose Stem Cells Whether the adipose tissue-derived multipotent mesenchymal stem cells obtained in Example 1 express the respective chemokine or growth factor receptors was examined using antibodies for the corresponding receptors by flow cytometry (FACS).

Meanwhile, the names of receptors and ligands for chemokines or growth factors are shown in Table 6 below.

TABLE 6

| Receptors | Chemokines or growth factors | Ligands |
|---|---|---|
| CCR1 | RANTES | CCL5 |
| CCR2 | MCP-1 | CCL2 |
| CCR7 | MIP-3β | CCL19 |
| CXCR4 | SDF-1α | CXCL12 |
| CXCR5 | BCA-1 | CXCL13 |
| CXCR6 | CXCL16 | CXCL16 |
| EGF | EGFR | |
| b-FGF | FGFR1 | |
| HGF | c-MET | |
| TGF-β1 | TGFBR2 | |
| IGF-1 | IGF1R | |
| PDGF-AB | PDGFRA, PDGFRB | |
| TNF-α | TNFRSF1A | |

Adipose stem cells were cultured in a T75 flask. When the cells reached a confluence of 90%, the cells were isolated by treatment with 0.25% trypsin/1 mM EDTA, after which the cells were washed with PBS and collected by centrifugation at 1,500 rpm for 5 minutes. The collected cells were immobilized with 10% FBS solution in a refrigerator at 4° C. for 1 hours or more, and then washed. Then, the cells were incubated with the antibodies shown in Table 7 below and were analyzed by FACS.

TABLE 7

| Antibodies | Brands | Serial Nos. |
|---|---|---|
| anti-human CCR1 | R&D Systems | MAB145 |
| anti-human CCR2 | R&D Systems | MAB150 |
| anti-human CCR7 | R&D Systems | MAB197 |
| anti-human CXCR4 | R&D Systems | MAB170 |
| anti-human CXCR5 | R&D Systems | MAB190 |
| anti-human CXCR6 | R&D Systems | MAB699 |
| anti-human EGF Receptor | BD Pharmingen | 555997 |
| TGFβ RII (D-2) | Santa Cruz Biotechnology | sc-1779949 |
| CD140a-PDGFRA | BD Pharmingen | 556002 |
| CD140b-PDGFRB | BD Pharmingen | 558821 |
| CD221-IGF1R | BD Pharmingen | 555999 |
| anti-human HGF R/c-MET | R&D Systems | FAB3582F |
| CD120a-TNFRSF1A | BD Pharmingen | 550514 |
| FGFR1 antibody [M19B2] | Abcam | ab823 |

Figure 6:
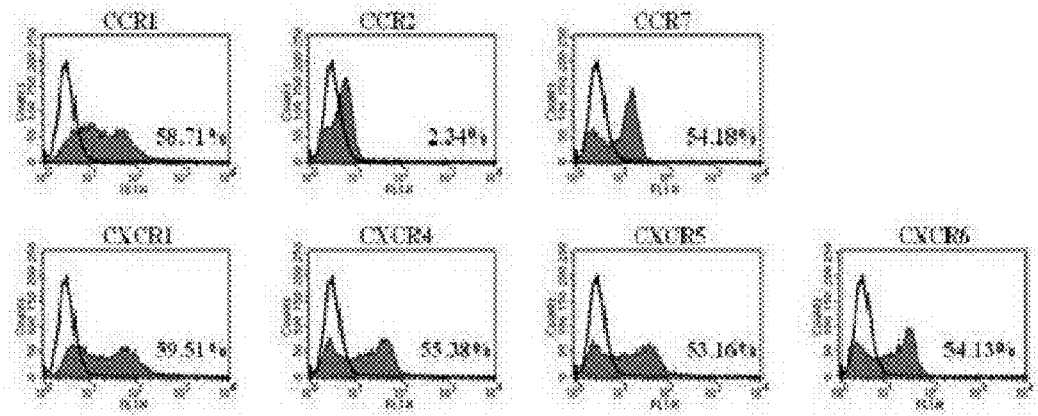
FIG. 6 is a set of graphs showing the results of FACS carried out to determine whether the receptors for various chemokines or growth factors are expressed in adipose tissue-derived multipotent mesenchymal stem cells and A549 cells.
Figure 6:
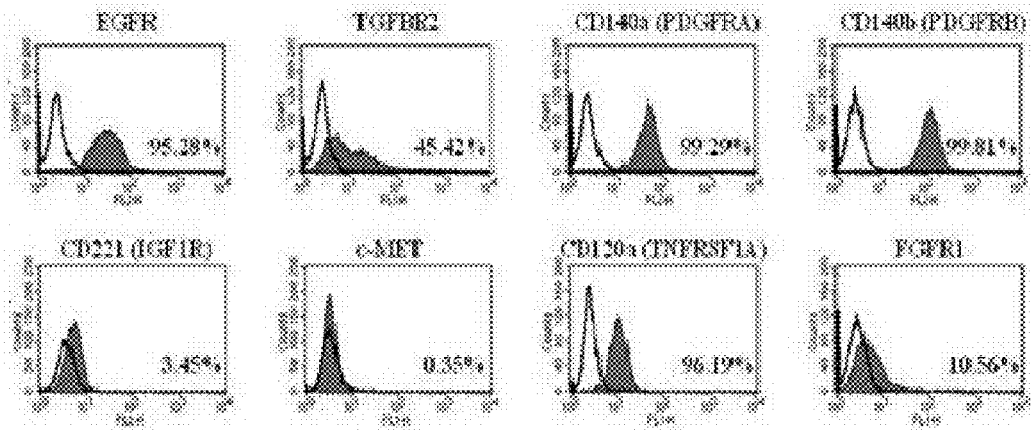
Figure 6:
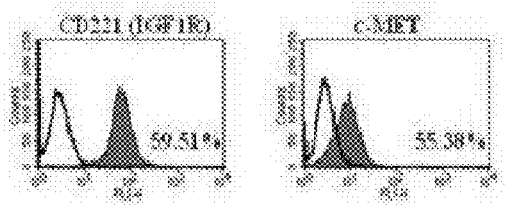

FIG. 6 shows the results of the analysis. In FIG. 6, the dark areas indicate the test group, and the black lines indicate the control group. The receptors for IGF-1 and HGF were not confirmed, and thus in order to confirm the function of the antibodies, the lung cancer A549 cell line purchased from a cell line bank was cultured and then analyzed by flow cytometry (FACS).

As can be seen from the results of FACS analysis shown in FIG. 6, the primed adipose tissue-derived multipotent mesenchymal stem cells expressed the receptors for Rantes (CCR1), MIP-3β (CCR7), SDF-1α (CXCR1), BCA-1 (CXCR5), CXCL16, EGF, TGF, PDGF-AB, IGF-1, TNF-α and FGF.

The above results confirmed that the receptors for specific chemokines or growth factors are expressed in adipose tissue-derived multipotent mesenchymal stem cells and that these receptors respond to the corresponding chemokines or growth factors and also that the expression levels of the receptors are increased by priming with the corresponding chemokines or growth factors. This suggests that the targeted migration of adipose tissue-derived multipotent mesenchymal stem cells to a disease site in vivo can be induced using the interaction between the chemokines or growth factors and their receptors, thereby effectively treating the disease corresponding to the disease site.

Example 7

Examination of mRNA of Chemokine or Growth Factor Receptors in Adipose Stem Cells Whether the adipose tissue-derived multipotent mesenchymal stem cells obtained in Example 1 express the mRNA of the respective chemokine or growth factor receptors was examined by RT-PCR.

Adipose stem cells cultured in a T75 flask were isolated by treatment with 0.25% trypsin/1 mM EDTA and then washed with PBS, after which the cells were collected by centrifugation at 1,500 rpm for 5 minutes. Total RNA was extracted from the collected cells using a total RNA extraction kit (iNtRON Biotechnology).

2 μg of the RNA was synthesized into cDNA using Maxime RT Pre-mix kit (iNtRON Biotechnology). 1 μl of the cDNA was denatured with 1×h-Taq buffer, 0.2 mM dNTP, 0.4 pM forward primer, 0.4 pM reverse primer, and 0.25 U/μl h-Taq DNA polymerase (Solgent) at 95° C. for 20 seconds, after which the primers were heated at each of the annealing temperatures shown in Table 8 for 40 seconds, and the PCR product was extended at 72° C. for 1 minute, thereby amplifying the cDNA. The PCR amplification was performed for 40 cycles. The heating temperatures of the receptor primers used in the PCR amplification are shown in Table 8 below.

TABLE 8

| Receptors | SEQ ID NOs.: 1 to 34 (F: forward, R: reverse) | Products | Annealing temperatures |
|---|---|---|---|
| CCR1 | F: 5'-CATCTTGGCTTCCATGCCAGGCT-3'<br>R: 5'-CCTCCGTCACTTGCACAGCCAGGT-3' | 380 bp | 62° C. |

TABLE 8-continued

| Receptors | SEQ ID NOs.: 1 to 34 (F: forward, R: reverse) | Products | Annealing temperatures |
|---|---|---|---|
| CCR2 | F: 5'-CCTCCTGACAATCGATAGATACCT-3'<br>R: 5'-GTCACCTGCGTGGCTTGGTCCAGT-3' | 474 bp | 56° C. |
| CCR7 | F: 5'-ATCTCCAAGACCAGAGATAGTG-3'<br>R: 5'-AAATGTTGCTCTCTTAACGAAT-3' | 461 bp | 62° C. |
| CXCR4 | F: 5'-GAGGAGTTAGCCAAGATGTG-3'<br>R: 5'-TTCTTCTGGTAACCCATGAC-3' | 489 bp | 62° C. |
| CXCR5 | F: 5'-CATCCTAATCATCCAATGCT-3'<br>R: 5'-AGCTCTTTTCTTCCCTCTGT-3' | 494 bp | 62° C. |
| CXCR6 | F: 5'-CCTTAACCCTGTGCTCTATG-3'<br>R: 5'-CTCACCTCTTCAACCTTCAG-3' | 517 bp | 62° C. |
| EGFR | F: 5'-GCATCTGCCTCACCTCCACCGTGCA-3'<br>R: 5'-GATTCCGTCATATGGCTTGGATCCA-3' | 419 bp | 64° C. |
| FGFR1 | F: 5'-CCTGACCACAGAATTGGAGGCTACA-3'<br>R: 5'-AGTTCATGTGTAAGGTGTACAGTG-3' | 250 bp | 58° C. |
| TGFBR2 | F: 5'-CCACGTGTGCCAACAACATCAACCA-3'<br>R: 5'-TGAAGAACGACCTAACCTGCTGCC-3' | 498 bp | 58° C. |
| CD120a-TNFRSF1A | F: 5'-GAGAGGCCATAGCTGTCTGG-3'<br>R: 5'-GTTCCTTTGTGGCACTTGGT-3' | 218 bp | 58° C. |
| CD140a-PDGFRA | F: 5'-GAAGCTGTCAACCTGCATGA-3'<br>R: 5'-CTTCTTTAGCACGGATCAGC-3' | 187 bp | 58° C. |
| CD140b-PDGFRB | F: 5'-GCGGCTGGTGGAGCCGGTGACTGA-3'<br>R: 5'-CTCACTTAGCTCCAGCACTCGGACA-3' | 508 bp | 68° C. |
| CD221-IGF1R | F: 5'-GTGAACGAGGCCGCAAGCATGCGT-3'<br>R: 5'-CTGTGGACGAACTTATTGGCGTTGA-3' | 299 bp | 58° C. |
| c-MET | F: 5'-CAGGCAGTGCAGCATGTAGT-3'<br>R: 5'-GATGATTCCCTCGGTCAGAA-3' | 201 bp | 58° C. |
| ADIPOR1 | F: 5'-GCTGACACGGTGGAACTGGCTGAACT-3'<br>R: 5-CTGTATGAATGCGGAAGATGCTCTTGA-3' | 337 bp | 60° C. |
| ADIPOR2 | F:5'-GGCAACATTTGGACACATCTCTTAGGT-3' | 538 bp | 60° C. |

TABLE 8-continued

| Receptors | SEQ ID NOs.: 1 to 34 (F: forward, R: reverse) | Products | Annealing temperatures |
|---|---|---|---|
| | R: 5-CAGCTCCTGTGATGTAGAGGCTGGCCA-3' | | |
| GAPDH | F: 5'-AATCCCATCACCATCTTCCAG-3'<br>R: 5'-AGGGGCCATCCACAGTCTTCT-3' | 362 bp | 55° C. |

Each of the PCR products was electrophoresed with a Sizer DNA Marker-50 (iNtRON) using 2.0% agarose gel and 1×TAE reagent at 110 V for 1 hour and 30 minutes, and then was imaged with Fuji molecular imaging software. As a control gene, GAPDH was used. All the PCR products were sequenced by Solgent Co., Ltd., and as a result, the PCR products were determined to have a sequence identity of 99% or higher.

Figure 7:
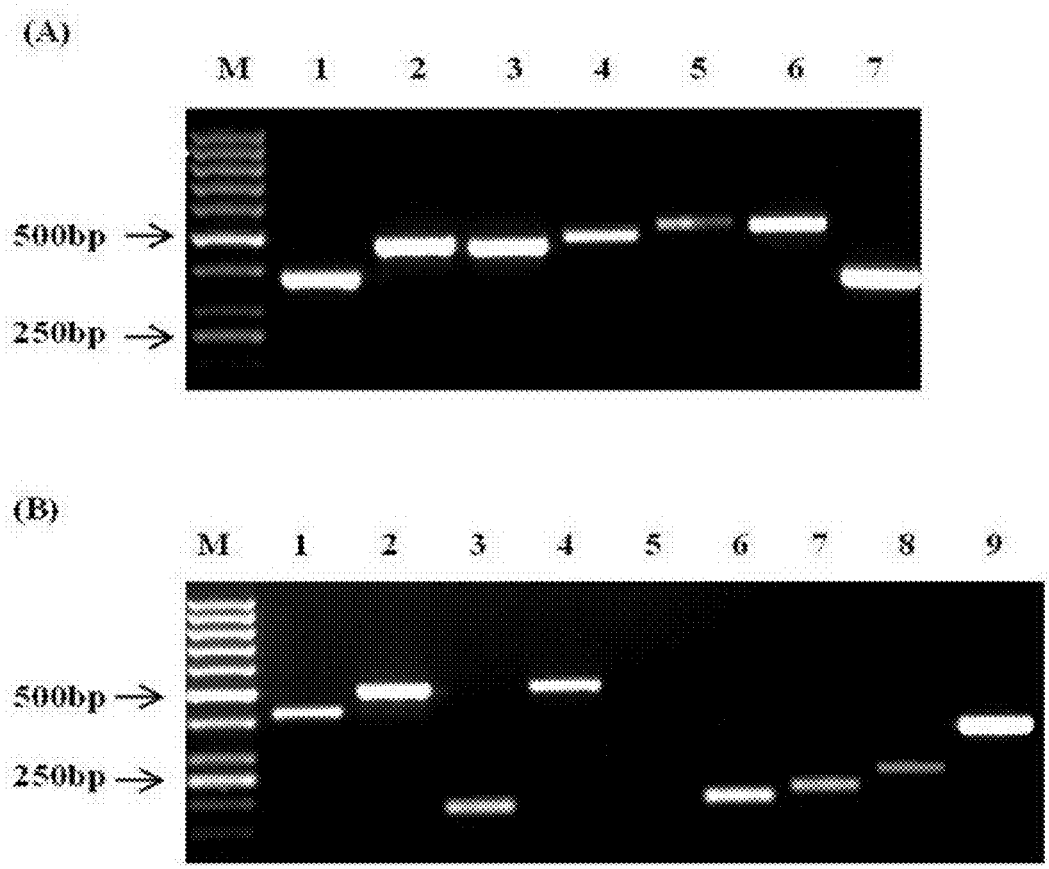
FIG. 7 is a set of photographs showing the results of RT-PCR carried out to determine whether the mRNA of the receptors for various chemokines or growth factors is expressed in adipose tissue-derived multipotent mesenchymal stem cells.

As can be seen from the results in FIG. 7, the mRNA of the receptors for chemokines or growth factors was expressed in the adipose stem cells. In FIG. 7A, lane 1: CCR1 (380 bp), lane 2: CCR2 (474 bp), lane 3: CCR7 (461 bp), lane 4: CXCR4 (489 bp), lane 5: CXCR5 (494 bp), lane 6: CXCR6 (517 bp), and lane 7: GAPDH (362 bp). In FIG. 7B, lane M: marker, lane 1: EGFR (419 bp), lane 2: TGFBR2 (498 bp), lane 3: PDGFRA (187 bp), lane 4: PDGFRB (508 bp), lane 5: IGF1R (299 bp; non-expressed), 6: c-MET (201 bp), lane 7: TNFRSF1A (218 bp), lane 8: FGFR1 (250 bp), and lane 9: GAPDH (362 bp). In this Example, GAPDH was used as a positive control group.

The above results confirmed that the mRNA of the receptors for specific chemokines or growth factors is expressed in the adipose stem cell. This suggests that the targeted migration of the adipose stem cells to a disease site in vivo can be induced using the interaction between the chemokines or growth factors and their receptors, thereby effectively treating the disease corresponding to the disease site.

Example 8

Priming of Adipose Stem Cells with Adiponectin and Examination of the Ability of Adiponectin to Induce Cell Migration at Various Concentrations 8-1: Examination of the Ability of Adiponectin to Induce Cell Migration at Various Concentrations The adipose tissue-derived multipotent mesenchymal stem cells isolated in Example 1 were primed with adiponectin for hours. The primed cells were induced to migrate by treatment with various concentrations (1 ng/ml, 10 ng/ml and 100 ng/ml) of adiponectin.

Figure 8:
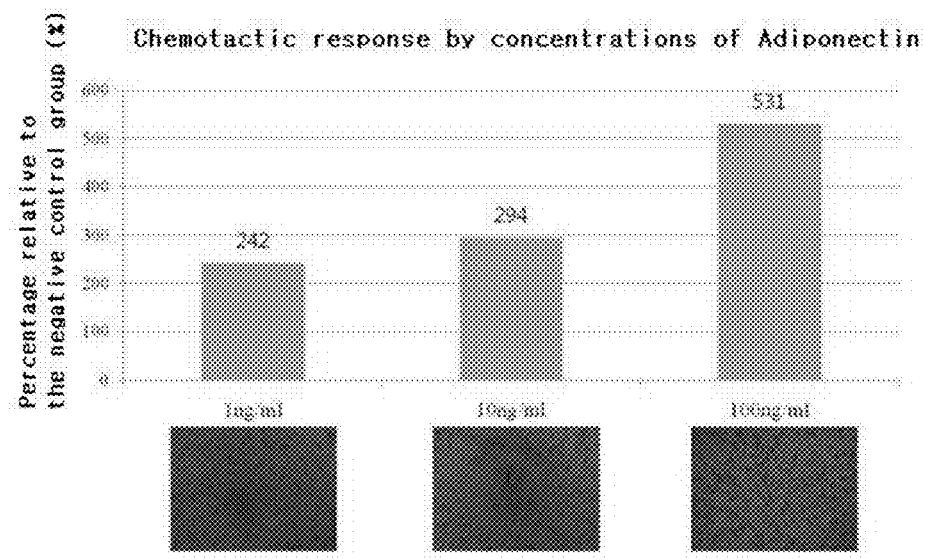
FIG. 8 depicts a graphic diagram and a set of micrographs, which show the results of inducing the migration of adipose tissue-derived multipotent mesenchymal stem cells, primed with adiponectin, using 1, 10 and 100 ng/ml of adiponectin.

FIG. 8 shows the results of induction of the cell migration. As can be seen therein, the migration of the cells treated with 100 ng/ml of adiponectin was about two times higher than that of the cells treated with 10 ng/ml of adiponectin. This suggests that the ability of adiponectin to induce cell migration increases as the concentration thereof increases.

8-2: Expression of Adiponectin Receptor in Adipose Stem Cells

Whether the adiponectin receptor is expressed in adipose stem cells was examined by RT-PCR in the same manner as in Example 7 using the primers and annealing temperatures shown in Table 8 above.

Figure 9:
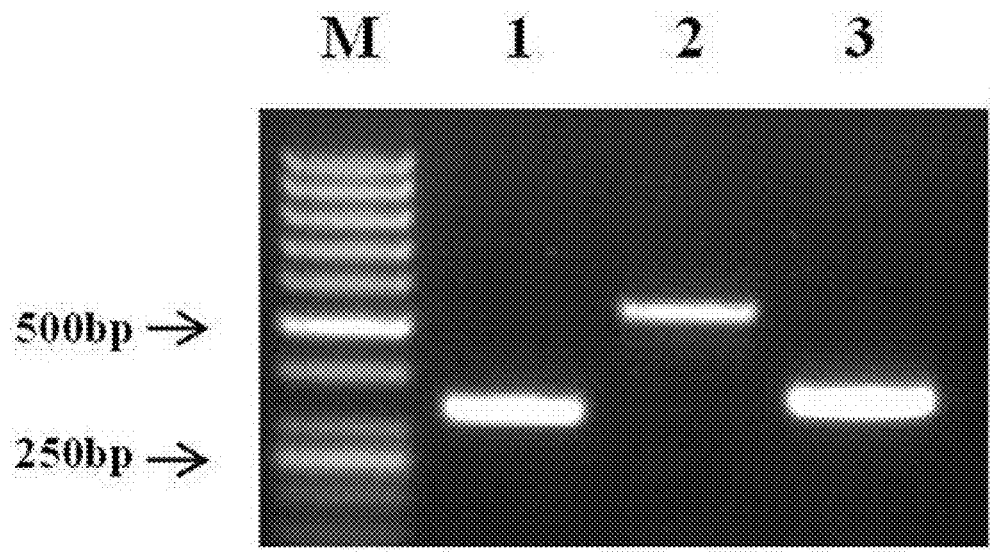
FIG. 9 is a set of photographs showing the results of RT-PCR carried out to determine whether the mRNA of adiponectin receptors 1 and 2 is expressed in adipose tissue-derived multipotent mesenchymal stem cells.

As a result, as can be seen in FIG. 9, two types of adiponectin receptors (1: ADIPOR1 (337 bp), and 2: ADIPOR2 (538 bp)) were expressed in the adipose stem cells. Thus, it was confirmed that priming of adipose cells with adiponectin leads to an increase in the expression level of the adiponectin receptor in the cells such that the interaction between adiponectin and the adiponectin receptor can be used to treat disease.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

The present invention relates to the ability of adipose-derived adult stem cells and their secretory products to migrate. According to the present invention, adipose-derived adult stem cells primed with a specific chemokine or growth factor or their secretory products can be administered by a simple method such as intravenous administration, and are able to target a disease site in need of transplantation of the stem cells and migrate to the disease site. Thus, the adipose-derived adult stem cells or their secretory products according to the present invention are very useful as a cell therapeutic agent that safely migrates to a disease site without a complex surgical operation and exhibits a treatment effect on the disease site.

The invention claimed is:

1. A method for inducing the migration of adipose tissue-derived adult stem cells, the method comprising the steps of:
    priming adipose tissue-derived adult stem cells by culturing the cells in medium with added adiponectin; and one or more factors selected from the group consisting of
    TNF-α (tumor necrosis factor-α), PDGF-AB (platelet derived growth factor AB)
    Rantes, SDF-1α (stromal cell-derived factor-1α), and MCP-1 (monocyte chemoattractant protein-1); and
    administering a composition containing the primed adipose tissue-derived adult stem cells into an in vivo site which is not in direct contact with a disease site.

2. The method of claim 1, wherein the step of administering is performed by intravenous administration.

3. The method of claim 1, wherein the cells were primed for 24 hours.

* * * * *

UNITED STATES PATENT AND TRADEMARK OFFICE
CERTIFICATE OF CORRECTION

PATENT NO. : 8,808,682 B2  
APPLICATION NO. : 13/502898  
DATED : August 19, 2014  
INVENTOR(S) : Ra et al.

It is certified that error appears in the above-identified patent and that said Letters Patent is hereby corrected as shown below:

In the Specification

Column 3, line 9: "protein-3M" should be -- protein-3β --.

Column 9, line 53: "μ1" should be -- $\mu\ell$ --.

Column 10, line 40: "m1" should be -- $m\ell$ --.

Column 11, lines 26 and 53: "μ1" should be -- $\mu\ell$ --.

Column 11, line 29: "m1" should be -- $m\ell$ --.

Column 12, line 16: "μ1" should be -- $\mu\ell$ --.

Column 14, lines 43 and 50: "μ1" should be -- $\mu\ell$ --.

Signed and Sealed this  
Twenty-eighth Day of October, 2014

Michelle K. Lee  
*Deputy Director of the United States Patent and Trademark Office*